(12) United States Patent
Prasad et al.

(10) Patent No.: US 9,222,907 B2
(45) Date of Patent: Dec. 29, 2015

(54) NANO-POROUS MEMBRANE BASED SENSORS

(71) Applicant: State of Oregon acting by and through the State Board of Higher Education on behalf of Portland State University, Portland, OR (US)

(72) Inventors: Shalini Prasad, Allen, TX (US); Ravi Kiran Kondama Reddy, Bend, OR (US)

(73) Assignee: State of Oregon acting by and through the State Board of Higher Education on behalf of Portland State University, Portland, OR (US)

(*) Notice: Subject to any disclaimer, the term of this patent is extended or adjusted under 35 U.S.C. 154(b) by 196 days.

(21) Appl. No.: 13/855,146

(22) Filed: Apr. 2, 2013

(65) Prior Publication Data

US 2013/0224765 A1    Aug. 29, 2013

Related U.S. Application Data

(63) Continuation of application No. 11/634,367, filed on Dec. 4, 2006, now Pat. No. 8,409,411.

(60) Provisional application No. 60/742,010, filed on Dec. 2, 2005, provisional application No. 60/778,636, filed on Feb. 27, 2006, provisional application No. 60/793,372, filed on Apr. 19, 2006.

(51) Int. Cl.
| | | |
|---|---|---|
| G01N 27/327 | (2006.01) | |
| G01N 27/416 | (2006.01) | |
| G01N 27/26 | (2006.01) | |

(52) U.S. Cl.
CPC ............ G01N 27/26 (2013.01); G01N 27/3278 (2013.01)
USPC ....... 205/792; 204/549; 204/403.03; 205/778

(58) Field of Classification Search
CPC   G01N 27/26; G01N 27/3275; G01N 27/3278
USPC .................. 204/403.01–403.15; 205/81, 792, 205/777.5, 778; 436/62–71, 500–548
See application file for complete search history.

(56) References Cited

U.S. PATENT DOCUMENTS

| | | |
|---|---|---|
| 5,670,031 A | 9/1997 | Hintsche et al. |
| 5,683,562 A | 11/1997 | Schaffar et al. |
| 6,682,648 B1 | 1/2004 | MacPhee et al. |
| 6,811,037 B2 | 11/2004 | Hintsche |
| 6,881,379 B1 | 4/2005 | Bredehorst et al. |
| 7,208,077 B1 | 4/2007 | Albers et al. |
| 2001/0019829 A1* | 9/2001 | Nelson et al. .................. 435/7.1 |

(Continued)

OTHER PUBLICATIONS

Li et al. "On the Growth of Highly Ordered Pores in Anodized Aluminum Oxide" Chem. Mater. 1998, 10, 2470-2480.*

(Continued)

*Primary Examiner* — Susan D Leong
(74) *Attorney, Agent, or Firm* — Klarquist Sparkman, LLP

(57) ABSTRACT

Sensors include nano-porous alumina membranes that are sensitized by immobilization of antibodies in the nano-pores. The nano-membranes can be sensitized to respond to a single target compound, or different portions of the nano-membrane can be differently sensitized. Capture of the target compound can be detected based on a spectral signature associated with electrical conductance in the nano-pores.

24 Claims, 9 Drawing Sheets

(56) References Cited

U.S. PATENT DOCUMENTS

| | | | |
|---|---|---|---|
| 2001/0021534 A1* | 9/2001 | Wohlstadter et al. | 436/518 |
| 2002/0009723 A1 | 1/2002 | Hefti | |
| 2002/0028475 A1 | 3/2002 | Ligler et al. | |
| 2002/0197622 A1 | 12/2002 | McDevitt et al. | |
| 2003/0032000 A1 | 2/2003 | Liu et al. | |
| 2003/0040466 A1 | 2/2003 | Vodyanoy et al. | |
| 2003/0219196 A1 | 11/2003 | Weng et al. | |
| 2004/0029259 A1 | 2/2004 | McDevitt et al. | |
| 2005/0226884 A1* | 10/2005 | Price et al. | 424/155.1 |
| 2006/0134820 A1 | 6/2006 | Tang et al. | |

OTHER PUBLICATIONS

Arenkov et al., "Protein microchips: use for immunoassay and enzymatic reactions," *Anal. Biochem.* 278:123-131, 2000.

Ball, "Electrochemical nanoliter vials and magnetoelastic films as sensing platforms," *Dissertation*, University of Kentucky 2003.

Buffon et al., "Widespread coronary inflammation in unstable angina," *N. Engl. J. Med.* 347:5-12, 2002.

Calvert et al., "Toughness in synthetic and biological multilayered systems," *Philos. Transact. A. Math. Phys. Eng. Sci.*, 360(1791):199-209, 2002.

Campagnolo et al., "Real-time, label-free monitoring of tumor antigen and serum antibody interactions," *J. Biochem. Biophys. Methods* 61:283-298, 2004.

Chen et al., "An investigation of the mechanisms of electronic sensing of protein adsorption on carbon nanotube devices," *J. Am. Chem.* 126(5):1563-1568, 2004.

Chou et al., "Development of an immunosensor for human ferritin, a nonspecific tumor marker, based on surface plasmon resonance," *Biosens. Bioelectron.* 19:999-1005, 2004.

Cui et al., "Nanowire nanosensors for highly sensitive and selective detection of biological and chemical species," *Science* 293:1289-1292, 2001.

Danesh et al., "Association of fibrinogen, C-reactive protein, albumin, or leukocyte count with coronary heart disease: meta-analyses of prospective studies," *JAMA* 279:1477-1482, 1998.

Dodabalapur et al., "Physics and applications of organic microcavity light emitting diodes," *J. Appl. Phys.* 80:6954-6964, Dec. 1996.

Etzioni et al., "The case for early detection," *Nature Reviews* 3:1-10, Apr. 2003.

Fawcett, "Dipole0dipole interactions and their role in relaxation processes in polar solvents," *Chem. Phys. Lett.* 174:167-175, 1990.

Fisher et al., "Electroluminescence from a conjugated polymer microcavity structure," *Appl. Phys. Lett.* 67:1355-1357, Sep. 1995.

Hahm et al., "Direct Ultrasensitive Electrical Detection of DNA and DNA Sequence Variations Using Nanowire Nanosensors," *Nano Letters* 4:51-54, 2004.

Jordan et al., "Efficiency enhancement of microcavity organic light emitting diodes," *Appl. Phys. Lett.* 69:1997-1999, Sep. 1996.

Mangano, "Perioperative Medicine," NHLBI Working Group Deliberations and Recommendations, *J. Cardiothoracic and Vascular Anesthesia* 18:Feb. 1-6, 2004.

Masuda et al., "Highly ordered nanochannel-array architecture in anodic alumina," *Appl. Phys. Lett.* 71:107-112, Nov. 1997.

Ozin, "Nanochemistry: synthesis in diminishing dimensions," *Adv. Mater.* 4:612-649 1992.

Padigi et al., "Micro-photonic cylindrical waveguide based protein biosensor," *Nanotechnology* 17:4384-4390, 2006.

Peng et al., "P-78: Design and Characterization of Organic Light Emitting Diodes with Microcavity Structure," *SID 03 Digest*, pp. 513-518, 2003.

Prasad et al., "Development of nanostructured biomedical micro-drug testing device based on in-situ cellular activity monitoring," *Biosens. Bioelectron.* 21:1219-1229, 2006.

Prasad et al., "Neuron-based microarray sensors for environmental sensing," *Electrophoresis* 25:3746-3760, 2004.

Routkevitch et al., "Electrochemical fabrication of the nano-wire arrays: template, materials and applications," in Andricacos, P.C., Corcoran, S.G., Delplancke, J.L., Moffatt, T.P., P.S. (Eds.), *Proceedings of the Electrochemical Synthesis and Modification of Materials Symposium*, Boston, MA, Materials Research Society, Pittsburgh, 1997.

Sander, "Genomic medicine and future of health care," *Science* 287:1977-1978, Mar. 2000.

Schonbeck et al., "CD40 signaling and plaque instability," *Circ Res* 89:1092-1103, 2001.

Smith et al., "Multicolor quantum dots for molecular diagnostics of cancer," *Expert Rev. Mol. Diagn.* 6:231-244, 2006.

Srivinas et al., "Trends in research for cancer detection," *Lancet Oncol.* 2:695-704, 2001.

Suefuji et al., "Increased plasma tissue factor levels in acute myocardial infarction," *Am. Heart J.* 134:253-259, 1997.

Suzuki et al., "Diagnostic implications of circulating oxidized low density lipoprotein levels as a biochemical risk marker of coronary artery disease," *Clin. Biochem.* 35(5):347-353, 2002.

Takhistov, "Electronchemical synthesis and impedance characterization of nano-patterned biosensor substrate," *Biosens. Bioelectron* 19:1445-1456, 2004.

Tang et al., "Organic electroluminescent diodes," *Appl. Phys.* 51:913-915, Sep. 1987.

Tsutsui et al.., "Sharply directed emission in organic electroluminescent diodes with an optical-microcavity structure," *Appl. Phys. Lett.* 65:1868-1870, Oct. 1994.

Wee et al., "Novel electrical detection of label-free disease marker proteins using piezoresistive self-sensing micro-cantilevers," *Biosens Bioelectron* 20:1932-1938, 2005.

Zheng et al., "Multiplexed electrical detection of cancer markers with nanowire sensor," *Nature* 23:1294-1301, 2005.

Zrenner et al., "Spatially resolved magneto-optics on confined systems," *Phys. B.* 256:300-307, 1998.

* cited by examiner

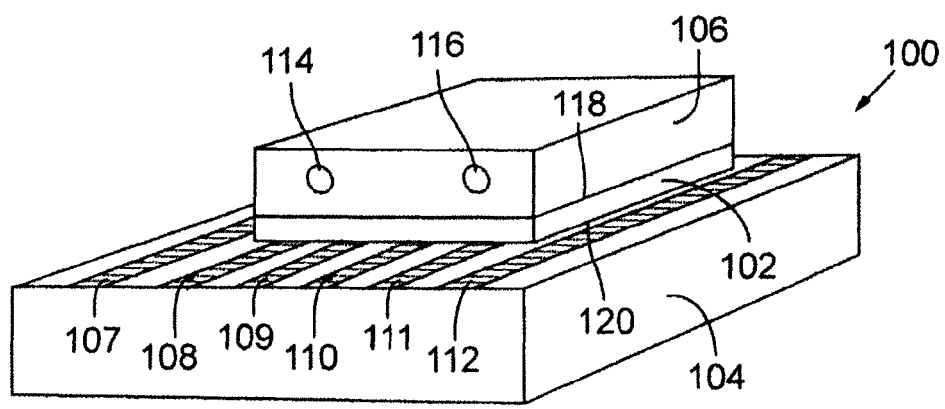
FIG. 1
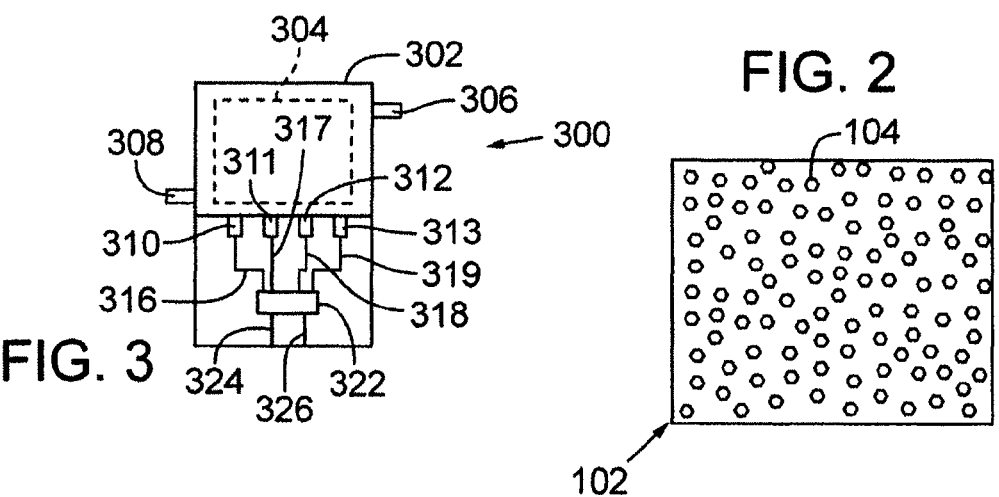
FIG. 3
FIG. 2
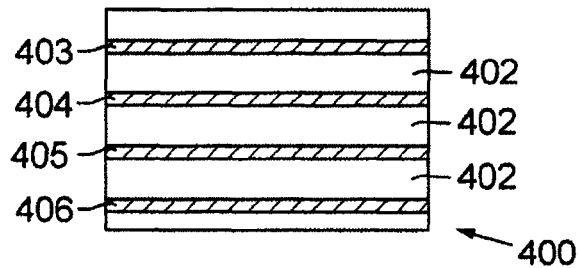
FIG. 4

NANO-POROUS MEMBRANE BASED SENSORS

CROSS REFERENCE TO RELATED APPLICATIONS

This application is a continuation of U.S. patent application Ser. No. 11/634,367, filed on Dec. 4, 2006, which claims the benefit of U.S. Provisional Application No. 60/742,010, filed Dec. 2, 2005, U.S. Provisional Application No. 60/778,636, filed Feb. 27, 2006, and U.S. Provisional Application No. 60/793,372, filed Apr. 19, 2006, all of which are incorporated herein by reference.

ACKNOWLEDGMENT OF GOVERNMENT SUPPORT

This invention was made with government support under N00014-07-1-0457 awarded by the Office of Naval Research. The government has certain rights in the invention.

FIELD

The disclosure pertains to nano-porous membrane based sensors and other biosensors.

BACKGROUND

Genomics and proteomics research has identified biomarkers that can be used in the detection and treatment of many diseases. Disease assessment can be based on one or many biomarkers, and in some cases, different biomarkers may be appropriate for different disease stages. Such biomarkers can be used to assess disease progress and aid in determining treatment as well as in judging the effectiveness of a course of treatment. Accordingly, biomarker based measurements can permit improved patient care.

Unfortunately, biomarker based measurements can be slow, expensive, or otherwise impractical. Conventional methods used with biomarkers are typically based on gel electrophoresis, enzyme-linked immunosorbent assays (ELISAs), plasma resonance, or other techniques. These methods generally have limited sensitivity, slow response, and lack specificity. Thus, although biomarkers offer promise for improved disease treatment and diagnosis, these advantages have not been realized in practice, and improved methods and apparatus are needed.

SUMMARY

Biomarker detectors can be fabricated to include a plurality of nano-pores formed in a suitable substrate. Such nano-pores can be arranged in regular patterns, irregularly, or can be randomly distributed. The nano-pores can be of similar sizes (length, cross-sectional area), or different sizes or a selected distribution of sizes can be provided in a single substrate. Nano-pores typically have cross-sectional areas similar to the cross-sectional areas of cylinders having diameters of between about 5 nm and 1000 nm. Nano-pore aspect ratios (length/diameter) typically are in a range from about 0.5 to 1000. Dimensions, shapes, and aspect ratios can be selected based on a particular application. Nano-pore cross-sectional areas can be rectangular, hexagonal, circular, elliptical, or other shape. Nano-porous membranes can be used for specimen analysis based on, for example, sample size and structure (size based filtration) or based on nano-pore sensitization using antibodies or other sensitizing agents.

Nano-porous membranes are formed by providing a substrate with a plurality of nano-pores. In some examples, a substrate includes nano-pores that are all of the same size, arranged in a series of rows and columns, but other arrangements of pores of the same or different sizes can be used. Nano-pores in one or more regions of the membrane are electrically connected to a readout amplifier, typically a differential amplifier that can produce a signal based on a difference in an electrical characteristic of the nano-pores in the different regions. The electrical readout can be processed to obtain, for example, a spectrum (using, for example, a fast Fourier transform), a power spectral density, or to identify a particular spectral component associated with an intended response. The electrical readout can be configured to permit measurement of a time evolution of response so that, for example, spectrum as a function of exposure time is determined.

Substrates are generally selected for ease of nano-pore formation. Aluminum is convenient as it can be electrochemically processed to produce alumina nano-pores of hexagonal cross-sectional area, and having different aspect ratios. Aspect ratios (length/diameter) of at least about 1000:1 can be achieved. Aperture dimensions can be configured based on electrochemical bath temperature and composition, applied voltage, current density, and/or exposure duration. Different aperture dimensions can be provided on a single substrate by selectively processing different substrate regions. Different size pores can be particularly useful in sized-based protein trapping in which the response of different pore sizes can be associated with protein size or other analyte property. For electrical measurements, the substrate is preferably substantially non-conductive, although configurations in which the nano-pores are electrically isolated from the substrate can be used as well. Substrates such as silicon, silicon oxides and nitrides can also be used, and apertures can be formed by wet or dry etching, ion beam milling, or other process. Surface portions of the substrate can be coated with a conductive material such as platinum, gold, silver, copper, or other material by sputtering, evaporation, or other processes so as to electrically couple a pluralities of nano-pores forming sets of nano-pores. In typical examples, antibodies or other sensitizing agents are immobilized on surfaces of the nano-pores, typically nano-pore sidewalls.

In representative examples, sensors comprise a substrate having defined therein at least one nano-porous membrane portion that includes a plurality of nano-pores. A first conductor is electrically coupled to a first set of nano-pores defined in the membrane, and a first sensitizing agent is immobilized at the first set of nano-pores. In further examples, a second conductor is electrically coupled to a second set of nano-pores, and a second sensitizing agent is immobilized at the second set of nano-pores. In some examples, the first sensitizing agent and the second sensitizing agent are the same or the first sensitizing agent and the second sensitizing agent are different. In additional examples, sensors further comprise a base substrate, wherein the first and second conductors are defined on the base substrate. In other examples, a spectrum analyzer is in communication with the first and/or second conductors and is configured to produce an estimate of a received signal portion associated with a signature frequency or frequencies. In additional examples, the spectrum analyzer is configured to produce an estimate of a received signal portion associated with at least two frequencies associated with a first signature and a second signature.

Sensor methods comprise administering a test specimen to an assembly of nano-pores sensitized to a selected target compound, and evaluating an electrical signal associated with administration of the test specimen to the nano-pores. The test specimen can be assessed based on the evaluation. In some examples, the electrical signal is evaluated to identify a magnitude of at least one electrical spectral peak associated with exposure of the sensitized nano-pores to the target compound, and the test specimen is assessed based on the magnitude. In further examples, the electrical signal is evaluated to identify an electrical signature associated with the target compound, and the test specimen is assessed based on the signature. According to some examples, the signature includes at least two electrical frequency components. In additional examples, the test specimen is administered to an assembly of nano-pores sensitized to at least a first and a second target compound. A first electrical signal and a second electrical signal are associated with a first set of nano-pores sensitized to the first target compound and a second set of nano-pores associated with the second target compound, respectively, and the test specimen is evaluated based on electrical signatures associated with the first target compound and the second target compound. In one example, the first target compound is C-reactive protein (CRP) and the second compound is myeloperoxidase (MPO).

Sensors are described herein that include a first conductor electrically coupled to a first set of sensitized nano-pores, and a signature analyzer electrically coupled to the first conductor, wherein the signature analyzer is configured to estimate at least one signature portion based on an electrical signal coupled from the first conductor. In some examples, the signature portion is a signal magnitude in a selected frequency range. A signature database can be provided, and the signature analyzer configured to produce an indication of a presence or concentration of at least one analyte based on a comparison of the at least one signature portion with at least one stored signature.

A representative sensor comprises a base substrate having a plurality of conductor segments defined thereon, and a nano-porous membrane secured to the base substrate. The nano-porous membrane includes a plurality of sets of sensitized nano-pores electrically coupled to corresponding conductor segments. A fluid chamber is configured to receive a test fluid and communicate the test fluid to the sets of sensitized nano-pores. In an exemplary embodiment, the nano-porous membrane is an alumina membrane having a plurality of nano-pores with effective diameters in a range of about 5 nm to about 500 nm. In some examples, the first set of nano-pores has an effective diameter that is larger than an effective diameter of the second set of nano-pores.

Methods of fabricating alumina nano-porous membranes comprise selecting a pore size and exposing an aluminum substrate to an electrolyte bath, wherein a composition and temperature of the electrolyte bath are based on the selected pore size. In some examples, nano-pores of different effective diameters are produced by increasing an extent to which an aluminum substrate is immersed in the electrolyte bath while varying bath temperature or composition. In some examples, the extent is increased in steps or substantially continuously.

The foregoing and other objects, features, and advantages of the disclosed technology will become more apparent from the following detailed description, which proceeds with reference to the accompanying drawings.

BRIEF DESCRIPTION OF THE DRAWINGS

FIG. 1 is a schematic diagram of a sensor that includes a nano-membrane secured to a base substrate.

FIG. 2 is a schematic representation of a surface of an alumina nano-membrane.

FIG. 3 is a schematic diagram of a sensor that includes a plurality of sensitized regions.

FIG. 4 is a schematic diagram of a surface of a base substrate configured for attachment of an alumina nano-membrane.

DETAILED DESCRIPTION

Figure 5A:
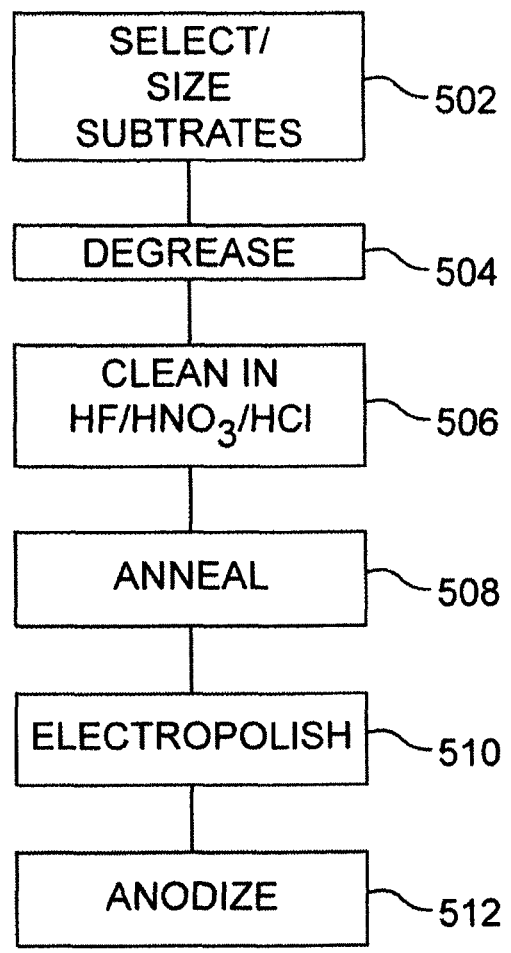
FIG. 5A is a block diagram of a representative method of forming alumina nano-membranes.

As used in this application and in the claims, the singular forms "a," "an," and "the" include the plural forms unless the context clearly dictates otherwise. Additionally, the term "includes" means "comprises." Further, the term "coupled" means electrically, electromagnetically, or fluidically coupled or linked and does not exclude the presence of intermediate elements between the coupled items.

The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Referring to FIG. 1, a sensor 100 includes a nano-membrane 102 (described in detail below) that is secured to a base substrate 104. A fluid chamber 106 is placed on the nano-membrane 102, and includes an inlet port 114 and an exit port 116 and is situated so that a first surface 118 of the nano-membrane is exposed to reagents provided to the fluid chamber 106 through the inlet port 114. Fluid chamber volume can be selected based on, for example, a convenient specimen volume, and is typically between about 1 μl and 1000 μl. Conductor strips 107-111 are provided on the base substrate 104, and are electrically coupled to respective portions of a second surface 120 of the nano-membrane 102. The nano-membrane 102 includes a plurality of nano-pores that couple the first and second surfaces 118, 120. For convenience, the conductors 107-111 are shown as linear segments that are covered by the nano-membrane 102 but that extend on both sides of the nano-membrane 102. In other examples, different conductor shapes can be used, and the conductors need not extend on both sides (or either side) of the nano-membrane. In other examples, electrical connections can be made through the base substrate. As shown in FIG. 1, a conductor strip 112 is provided as a reference conductor, and is not directly electrically coupled to the nano-membrane 102. Other conductors or additional conductors can be configured as reference conductors as well by, for example, coupling such conductors to unsensitized nano-pores in the nano-membrane or to nano-pores that are blocked to remain unaffected by specimen portions in the fluid chamber 106.

In a convenient example, the nano-membrane 102 is an alumina membrane formed from an aluminum foil, and gold conductor strips are patterned and formed on the base substrate 104 using contact photolithography. Other membrane materials can be used, and conductors of silver, gold, copper, or other conductor or semi-conductor materials can be used. The fluid chamber is formed of polydimethoxysilane (PDMS), but other materials can be used. Alternatively, the chamber 106 can be omitted and test materials dispensed directly onto the first surface of the nano-membrane 102.

FIG. 2 is a schematic representation of a surface of a nano-membrane 102. The nano-membrane 102 typically includes a plurality of pores 104 having effective diameters of about 10 nm to 500 nm. The pores can have circular, elliptical, hexagonal, cross-sections, or cross-sections of other shapes. In certain applications, pore diameter is substantially uniform or variable within a predetermined range. The nano-membrane 102 is preferably an electrical insulator so that the pores 104 are not electrically coupled to each other absent addition electrical connections such as the conductor strips 107-111.

The base substrate 104 is generally an insulator, or includes an insulator portion. For example, silicon with an oxide layer can serve as the base substrate, wherein the conductor strips are defined on or in the oxide layer so as to be substantially electrically isolated. Such a base substrate can be especially convenient for inclusion of detection electronics in the base substrate. However, other substrate materials such as glass, fused silica, polycarbonate, polyimides, ceramics, epoxy, plastics, or the like can be used.

In an example, the base substrate is formed using a 2 cm by 2 cm section of silicon wafer cleaved from a larger wafer. This substrate is cleaned in piranha solution, spin coated with a positive photoresist, and a quartz photomask is used to define features 1 μm by 2 cm. A 10 nm thick gold film is sputter coated onto the photoresist, and gold conductor strips 2 μm by 2 cm can be formed using a lift off process. FIG. 4 illustrates conductive strips 403-406 with gaps 402 formed on a surface of a base substrate 400.

FIG. 3 is a schematic view of a representative multi-analyte sensor 300 that includes a membrane 304 secured to a base substrate 302. Fluid ports 306, 308 are configured to direct samples to the membrane 304. The membrane has sets of pores that are coupled to respective conductors 310-313 defined on the base substrate 302. The conductors 310-313 are electrically coupled to a multiplexer or switch 322 via interconnections 316-319 that can be conductor segments on the base substrate 302 or other electrical connections. The multiplexer 326 has signal outputs 322, 324 that are configured to provide electrical signals associated with selected sets of pores to a signal analysis system. Typically, a signal associated with a specific pore sensitization and a reference signal are provided.

Figure 8:
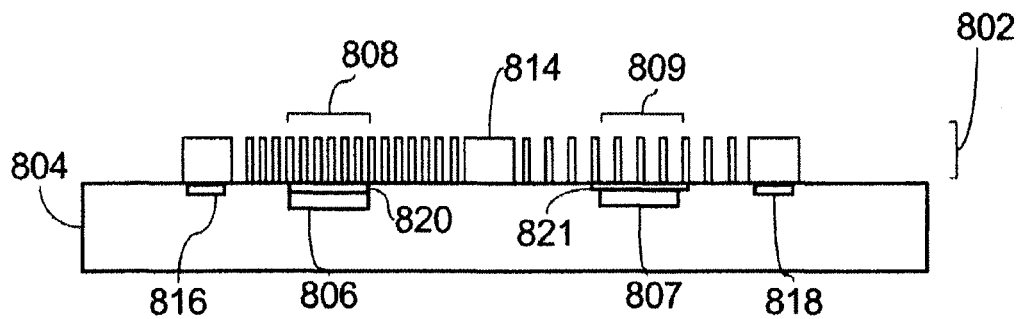
FIG. 8 is a schematic diagram of a sensor that includes a membrane secured to a base substrate.

FIG. 8 is a sectional view of a representative sensor that includes a nano-porous membrane 802 and a base substrate 804. The base substrate 804 includes conductor strips 806, 807 that are coupled to a first set 808 and second set 809 of nano-pores, respectively. The conductor strips are separated by additional nano-pores and a region 814 without nano-pores. The nano-membrane 802 is secured to the base substrate 804 with a conductive silver paint deposited at predetermined attachment locations 816, 818. In other examples, carbon paint, epoxies, heat bonding, or anodic bonding can be used. For adhesive bonding, a portion of the substrate is dedicated to bonding, and the substrate can be made larger that an intended active area to provide a bonding region. In a typical example, a width of the conductor strips is $10-10^4$ times smaller than the spacing between the conductor strips 806, 807 so that the nano-pores coupled to the conductor strips 806, 807 are electrically isolated, and electrical signals at the conductor strips 806, 807 depend only on electrical processes in the sets 808, 809. As shown in FIG. 8, sensitizing layers or sensitizing agents 820, 821 are situated at the conductors 806, 807, respectively, and on surfaces of the pores of the sets 808, 809. Different types of sensitizing agents can be used. For example, one or more antibodies or antibody compositions can be immobilized on the conductors or in the nanopores. As shown in FIG. 8, pores of different diameters are provided in a single membrane. In addition, conductors are shown as defined in a base substrate, but typically conductors are formed on a substrate surface.

Alumina Membrane Fabrication

A representative method of membrane fabrication is outlined in FIG. 5A. High purity aluminum foil substrates (99.99% pure) are selected and sized in a step 502, degreased in acetone in a step 504, and cleaned in an aqueous solution of HF, $HNO_3$, and HCl in a volume ratio of about 1:1:2.5 in a step 506. After cleaning, the substrates are annealed in a nitrogen ambient at 400° C. for about 45-60 min. in a step 508 to remove mechanical stresses and allow re-crystallization. Grain sizes can be measured using electron microscopy, and grain sizes in the annealed substrates are typically between about 100 nm and 200 nm. Surfaces of the annealed substrates are electro-polished in step 510 in a mixture of $HClO_4$ (perchloric acid) and $C_2H_5OH$ (ethanol). In a step 512, the substrates can be anodized at a constant cell potential in aqueous $H_2SO_4$ (sulfuric acid) at concentrations of between about 1.8 M and 7.2 M. Sulfuric acid/oxalic acid mixtures can also be used. Typical mixtures are combinations of 0.3 M oxalic acid with 0.18 M to 0.5 M sulfuric acid. Current densities typically range from about 50-100 $mA/cm^2$.

Multi-step anodizations can also be used. In a typical two step anodization, a first step is used to form a concave texture, and a second step is used to form nanostructures, typically at locations at which texture changes were formed in the first step. In a typical first anodization, the aluminum substrates are mounted on a copper plate anode, and a graphite plate is used a cathode. During anodization, the electrolyte is vigorously stirred and/or recycled, and cell voltage, current, and temperature are monitored and recorded. In this first anodization, cell potential is fixed at about 40 V and the substrates are exposed to 0.3 M oxalic acid ($H_2C_2O_4$) electrolyte solution for about 3 hrs at about 25° C. In a second anodization, partially anodized substrates are exposed to a mixture of 6% by weight of phosphoric acid and 1.8% by weight chromic acid for about 10 hrs at a temperature of about 60° C. After this second anodization, the first anodization is repeated for about 5 hrs. Pores are generally about 20 nm wide and about 25 nm deep. Any remaining aluminum in the substrates can be removed with a saturated mercuric chloride solution.

Figure 5B:
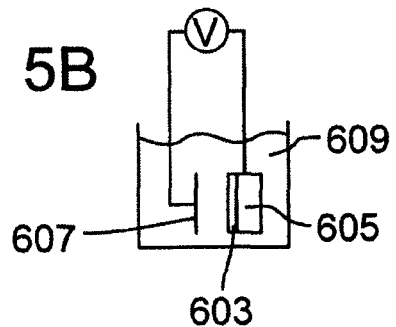
FIG. 5B illustrates exposure of an aluminum foil to an electrolyte bath for formation of an alumina nano-membrane.

FIG. 5B illustrates anodization. An aluminum substrate 603 is secured to a copper plate 605 that serves as an anode. A graphite plate 607 is used as a cathode, and the aluminum substrate/copper plate and graphite plate 607 are exposed to an electrolyte solution 609 at a selected applied voltage. Electrolyte solution temperature, composition, and concentration, and applied voltage are selected to provide an intended pore size, aspect ratio, and/or pore density.

In typical examples, nanopores having diameters of about 25, 50, and 100 nm are produced using cell voltages of about 12 V, 25 V, and 40 V, respectively, at a cell temperature of about 60° C. Current density varies from about 1.2 A/cm$^2$ to 5 A/cm$^2$. Pore densities can be varied from about $6 \cdot 10^8$/cm$^2$ to about $5 \cdot 10^{10}$/cm$^2$, and are typically directly proportional to current density and inversely proportional to cell temperature.

In the second anodization step, varying the electrolyte temperature from 25° C. to 50° C. in increments of 1° C. for every 10 minutes permits selection of pore widths in a range of about 12 nm to 200 nm. Varying the applied voltage from 40 V to 70 V at 5 V increments every 10 minutes permits selection of pore surface density in a range of about $10^5$ pores/mm$^2$ to $10^{15}$ pores/mm$^2$, and pore depth can be altered from about 10 nm to 250 nm by increasing the voltage. By varying the concentrations of oxalic, phosphoric and chromic acids from about (1:0.5:0.5) by volume to about (2:3:3) by volume, pore width can be varied from about 12 nm to 750 nm. Specific combinations of these conditions can be used to obtain selected pore dimensions and pore densities. These conditions are summarized in Table 1 below.

TABLE 1

Processing Ranges for Pore Width, Depth, and Density

| Parameter | Range (from) | Range (to) | Feature |
|---|---|---|---|
| Temperature | 25° C. | 50° C. | Pore width: 12 nm-200 nm |
| DC voltage | 40 V | 70 V | Pore depth: 10 nm-250 nm |
|  |  |  | Pore surface density: $10^5$ pores/mm$^2$ to $10^{15}$ pores/mm$^2$ |
| Acid ratio | 1:0.5:0.5 | 2:3:3 | Pore width: 12 nm to 750 nm |

Pores typically nucleate at surfaces of the substrates at approximately random locations, and pores have random locations and a broad distribution of sizes. Under certain specific conditions, a hexagonal ordering of pores is produced. These pores are well suited for trapping of nanometer sized particles. Pore sizes for a particular application can be selected based on a protein size so that the target protein "fits" the pores. Such a fit can reduce non-specific binding events, increasing measurement sensitivity and reliability.

Detection Methods

Figure 7:
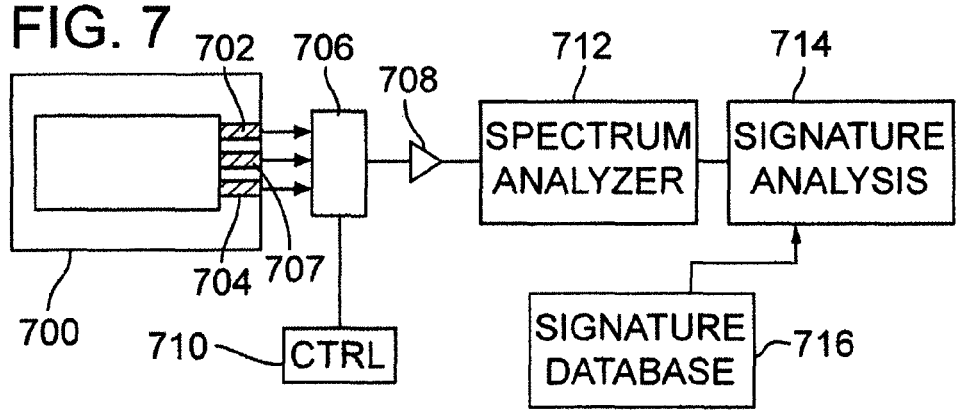
FIG. 7 illustrates a sensor apparatus that includes a sensor and a spectrum analysis system.

Sensors can be interrogated by coupling one or more conductor strips as shown in FIG. 7. A sensor 700 includes a plurality of conductors 702-704 that are coupled to a multiplexer 706 that selects one or more of the conductors for coupling to a buffer amplifier 708. The multiplexer 706 can be controlled for such selection based on a user selection or under control of a desktop, laptop, or palmtop computer indicated as a controller 710 in FIG. 7. Alternatively, each conductor can be coupled to a respective buffer amplifier, and signals on all conductors made simultaneously available for signal analysis. In other examples, a mechanical switch or probe can be used to selectively couple to one or more conductors.

The conductors 702-704 can be associated with different sensitizations (for example, contacted to nano-pores on which different types of antibodies are immobilized). Electrical signals from the conductors 702-704 are based on, for example, effective conductance variations associated with binding of antigen-antibody complexes. These electrical signals exhibit complex time domain behavior, but generally have characteristic features or "signatures" when viewed in the frequency domain. Typically, a specific bound complex is associated with one or more characteristic frequencies, and signal magnitude at the characteristic frequency (or frequencies) is a function of analyte concentration.

Characteristic frequencies can be detected with a spectrum analyzer 712 that is coupled to the selected conductor (or conductors) and that receives an electrical signal associated with the sensitized conductors/nano-pores. The spectrum analyzer 712 can be implemented using a mixer and a swept oscillator with a detector that is coupled to evaluate a magnitude and/or phase of a difference or sum frequency from the mixer. Alternatively, a time record of the coupled electrical signal can be stored, and a spectrum obtained using, for example, a fast Fourier transform. In some examples, a power spectrum is obtained in order to identify presence of a targeted material, or a response to a compound under investigation. A differential electrical signal is generally used such that a difference signal associated with a reference conductor and a conductor coupled to sensitized nano-pores is evaluated. Signals are generally available within seconds after exposure of a sensitized membrane to an analyte, and thus permit rapid analyte assessment. A signature analysis processor 714 is generally coupled to receive the detected spectra and, based on signatures stored in a signature database 716, determine presence and/or concentration of one or more analytes.

In one example, one or more specific protein biomarkers are bound to one or more nano-porous membranes that have been treated with an antibody receptor. Detected voltage variations are based on binding of the antibody-antigen protein complex to a base substrate. As an example, protein biomarkers associated with plaque rupture can be selected. These biomarkers can be used to assess perioperative ischemia which can be a predictor of surgical outcome. Selected biomarkers can be C-reactive protein (CRP) and myeloperoxidase (MPO). Purified samples of CRP, anti-CRP, MPO, and anti-MPO can be lyophilized from 0.01 M phosphate buffered saline solution (PBS) and 20 mM sodium acetate buffer, respectively, at a pH of about 7.2. CRP and MPR concentrations typically range from about 10 mg/ml to 50 ng/ml. Serum spiked samples include both proteins reconstituted in 20% human serum.

Base substrates and/or nano-porous membranes can be coated and incubated at about 37° C. for about 2 minutes. The base substrate can be selectively coated with bovine serum albumin (BSA) having a concentration of about 2 μg/ml in non-metallic areas and washed with PBS to reduce detection of non-specific binding. Pores can be selectively sensitized using micro injection techniques based on ink jet printing that can produce streamed liquid droplets in sizes ranging from about 1 µm to 5 µM. Volumes up to 500 ml can typically be dispensed from a single ink jet before ink jet replenishment is needed. Alternatively, antibodies in liquid form can be extracted from glass micro capillaries of pore widths of about 1-2 µm using vacuum suction. Extracted volumes are typically about 100 µL. Micro syringes can also be used to manually transfer specific antibodies to selected regions. Micro syringe volumes are typically about 5 µL.

Figure 9A:
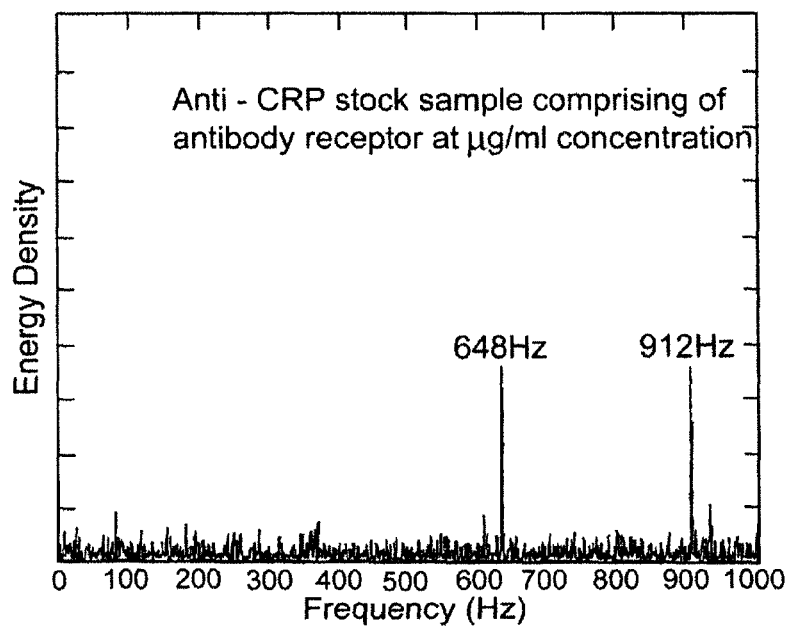
FIGS. 9A-9D illustrate spectra obtained with CRP antibody sensitized devices illustrating a detection signature based on spectral peaks at 362 Hz and 588 Hz.
Figure 9B:
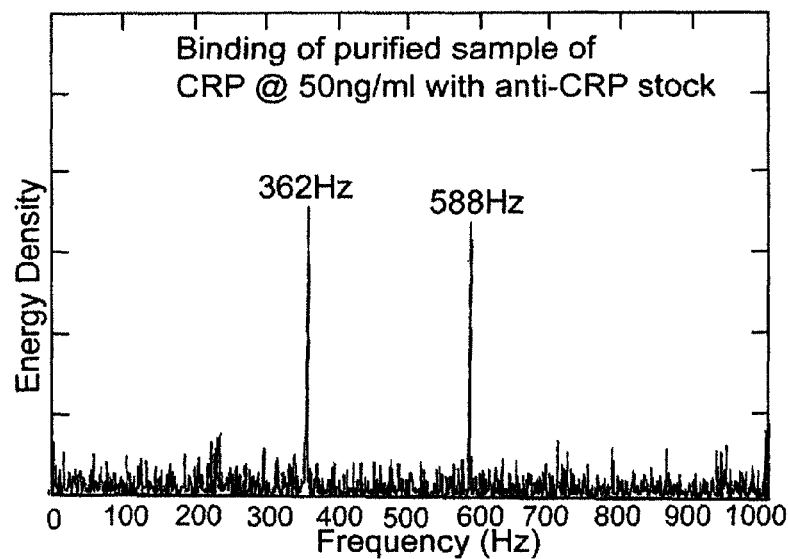
Figure 9C:
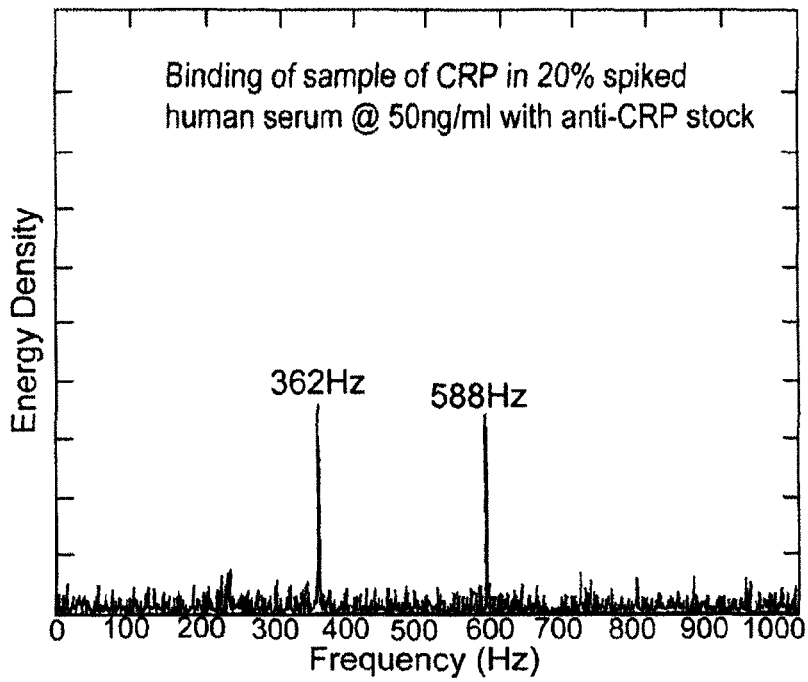
Figure 9D:
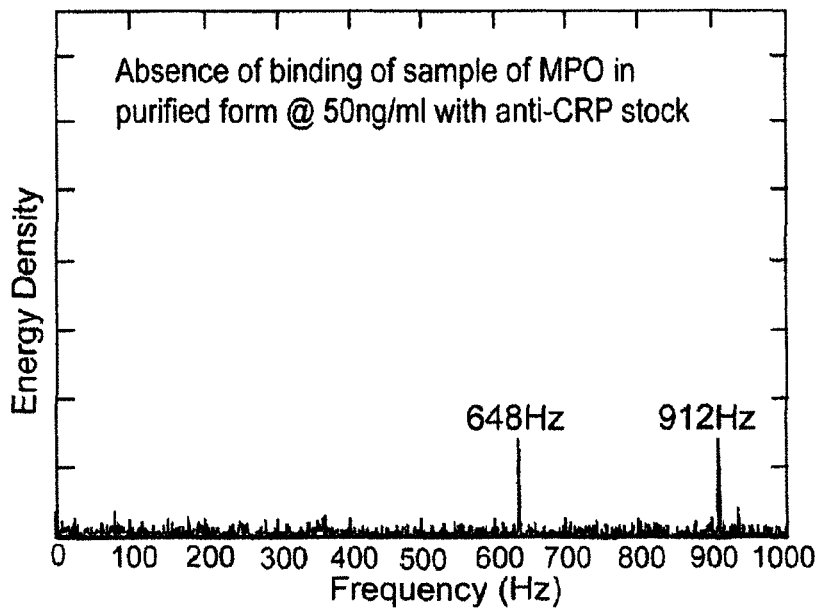

Response of sensors sensitized with CRP antibodies were measured with no additional analyte exposure, with exposure to test CRP samples, as well as an MPO containing specimen to determine non-specific binding. Representative spectra are illustrated in FIGS. 9A-9D. FIG. 9A illustrates response of a CRP antibody sensitized device (sensitized with a 1 µg/ml antibody solution) without analyte exposure. Characteristic spectral peaks are observed at 648 Hz and 912 Hz. FIGS. 9B-9C illustrate response of CRP antibody sensitized devices exposed to purified CRP samples (50 ng/ml) and a sample of CRP in 20% spiked human serum (50 ng/ml). Characteristic spectral peaks are apparent at 362 Hz and 588 Hz. FIG. 9D illustrates response of CRP antibody sensitized devices to purified MPO solution (50 ng/ml). The same spectral peaks as noted in FIG. 9A are apparent, indicating that MPO does not interfere with CRP detection.

Figure 10A:
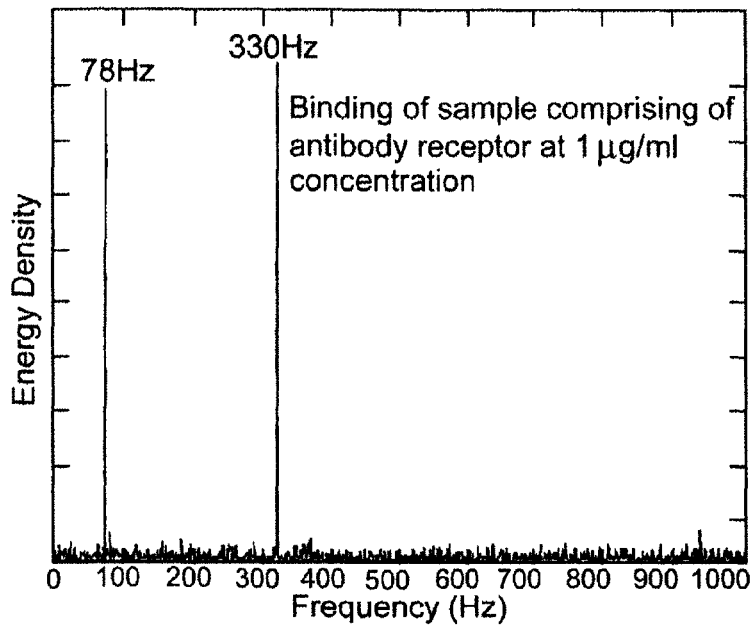
FIGS. 10A-10D illustrate spectra obtained with MPO antibody sensitized devices illustrating a detection signal based on spectral peaks at 180 Hz and 365 Hz.
Figure 10B:
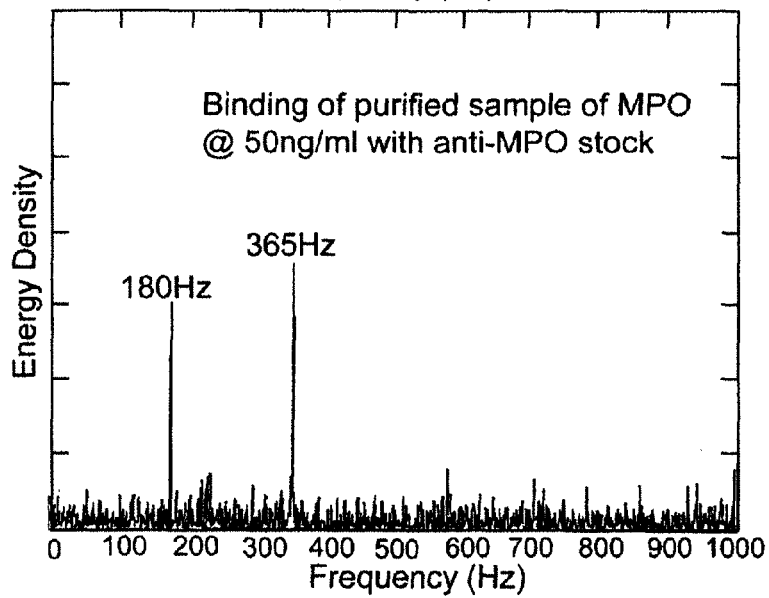
Figure 10C:
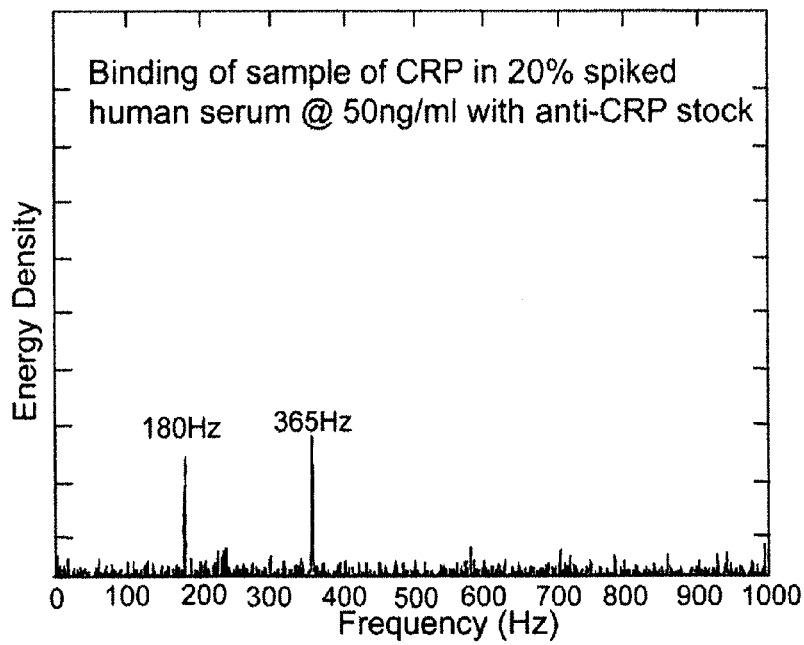
Figure 10D:
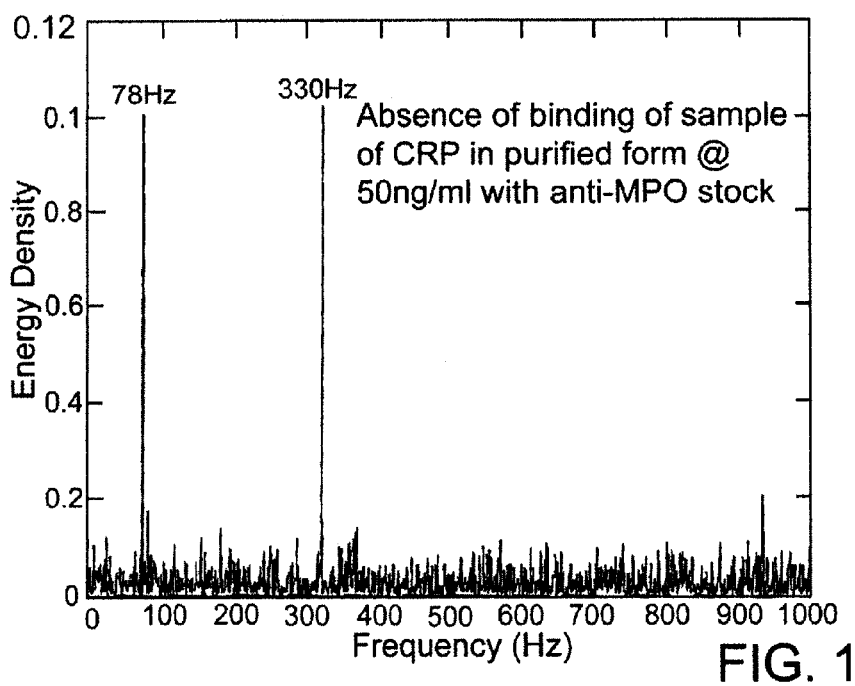

Similar results for MPO antibody sensitized devices are illustrated in FIGS. 10A-10D. FIG. 10A illustrates response of an MPO antibody sensitized device (sensitized with a 1 µg/ml antibody solution) without analyte exposure. Characteristic spectral peaks are observed at 78 Hz and 330 Hz. FIGS. 10B-10C illustrate response of MPO antibody sensitized devices exposed to a purified MPO sample (50 ng/ml) and a sample of MPO in 20% spiked human serum (50 ng/ml). Characteristic spectral peaks are apparent at 180 Hz and 365 Hz. FIG. 10D illustrates response of MPO antibody sensitized devices to purified CRP solution (50 ng/ml). The same spectral peaks as noted in FIG. 10A are apparent, indicating that CRP does not interfere with MPO detection. For both CRP and MPO sensitized devices, signal to noise ratio is a function of CRP or MPO concentration, respectively.

Response signatures are summarized in Table 2 below.

TABLE 2

MPO and CRP Signature Frequencies

| Antibody | Analyte | | |
|---|---|---|---|
| | CRP | MPO | None |
| Anti-CRP | 362/588 | 648/912 | 648/912 |
| Anti-MPO | 78/330 | 180/365 | 78/330 |

Additional Examples

Figure 6A:
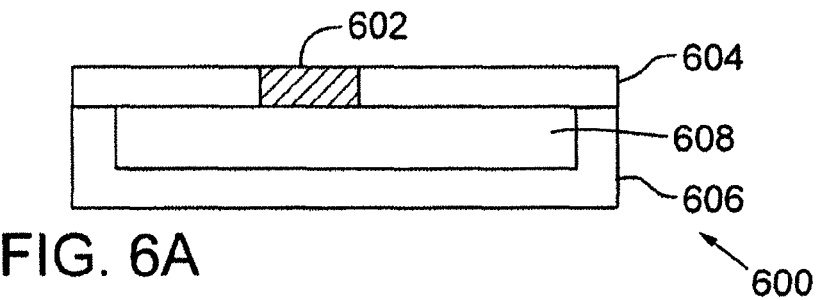
FIGS. 6A-6B illustrate a sensor that includes a nano-membrane retained in a channel in a silicon substrate.
Figure 6B:
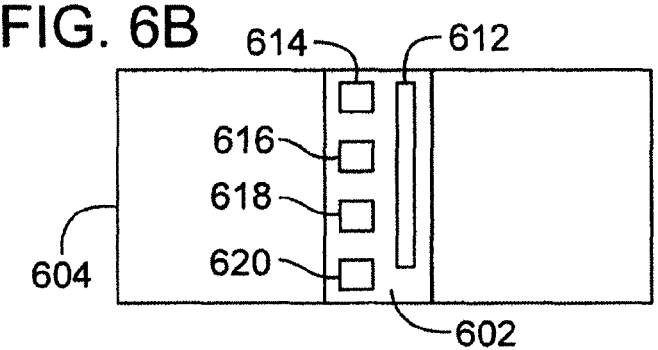

FIGS. 6A-6B construction of a sensor based on an alumina membrane 602 formed in a channel in a base substrate 604. The base substrate 604 is processed to define a channel in which aluminum is deposited. The aluminum is processed to form a nano-porous membrane, and portions of the base substrate are removed so that the alumina membrane extends completely through the remaining portion of the base substrate. A fluid chamber 608 is then defined with a channel piece 606. The base substrate and the channel piece are conveniently made of silicon for ease of manufacture.

As shown in FIG. 6B, conductors 612, 614, 616, 618, 620 can be used to define sensitized portions of the membrane 602. The membrane can be sensitized with, for example, antibodies. Alternatively, cells can be patterned onto the alumina membrane to investigate cell response to samples introduced into the chamber 606. For example, effects of a drug on a particular cell type can be investigated by recording electrical signals from the conductors 612, 614, 616, 618, 620 as a function of drug exposure.

Figure 11:
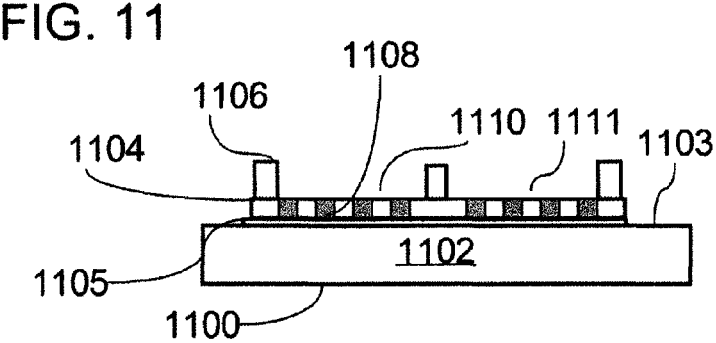
FIG. 11 is a sectional view of a representative sensor.

A sectional view of another representative sensor 1100 is provided in a FIG. 11. The sensor 1100 includes a supporting substrate 1102 that typically has a surface 1103 on which conductors for electrical connections to nano-pores 1108 in a nano-porous membrane 1104. Additional electrical circuit components can also be situated on the surface 1103, or the supporting substrate 1102 can be processed to include circuit components. Sidewalls 1106 are provided to define analyte wells 1110, 1111. In a typical application, an analyte is supplied to only one of the wells 1110, 1111 and a control reagent is applied to the other. The supporting substrate can be silicon or a silicon compound having copper, gold, or other conductors on the surface 203, but the supporting substrate can also be glass or fused silica with indium tin oxide (ITO) conductors. Other combinations of materials can be used as convenient. A patterned conductor layer 1105 is generally provided to, for example, combine electrical outputs associated with a single well, or nano-pores of selected characteristics such as size, aspect ratio, or sensitization reagent.

Figure 12:
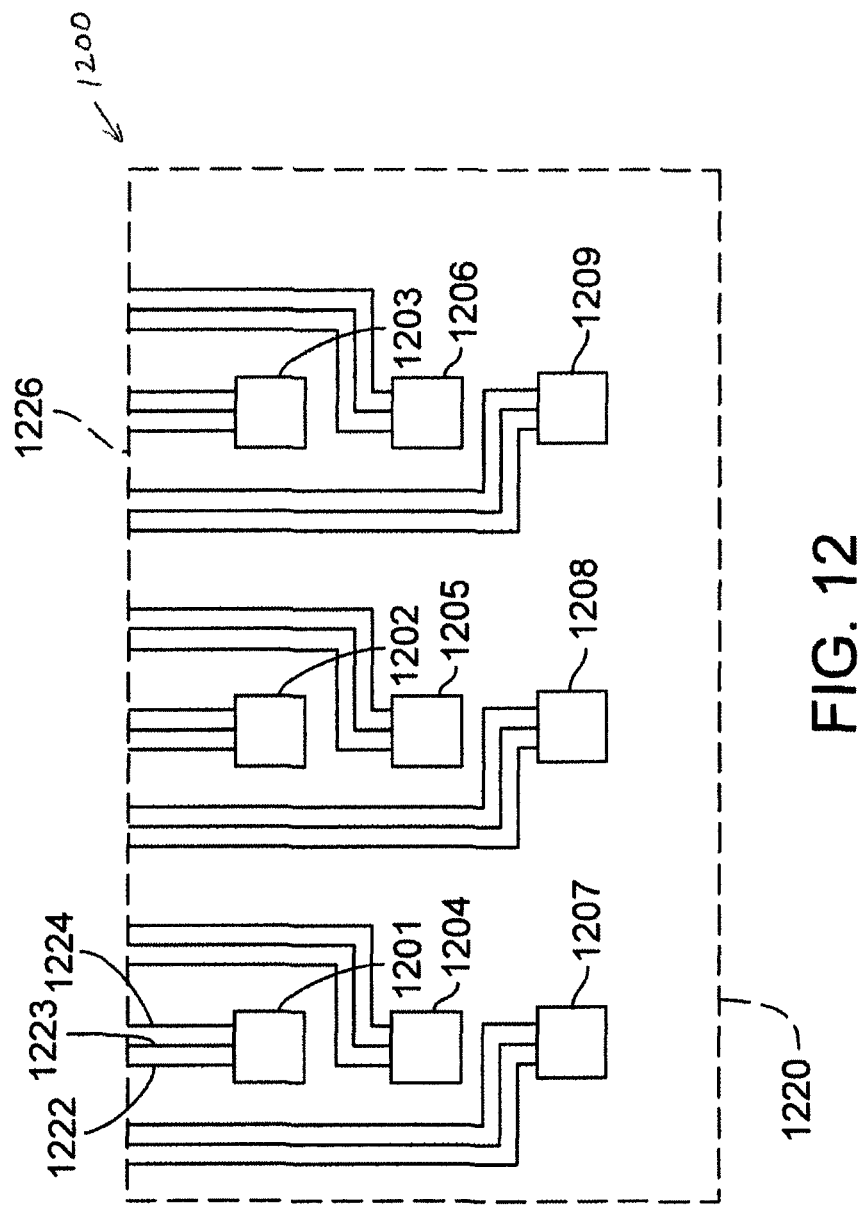
FIG. 12 illustrates a sensor assembly that includes an array of sensitized membrane sensors.

FIG. 12 illustrates a sensor assembly 1200 that includes an array of sensitized membrane sensors 1201-1209 situated in rows and columns on a substrate 1220. The sensors 1201-1209 include sensitized nano-porous membranes and base substrates that include electrical connections to the membranes. Each membrane can be sensitized and electrically connected for detection of a single analyte or a plurality of analytes. While nano-pores are typically sensitized for a single target analyte, interrogation using frequency domain signatures can permit a single nano-pore or set of nano-pores to be sensitized to a plurality of target analytes. As shown in FIG. 12, the sensor 1201 is coupled to conductors 1222, 1223, 1224 to accommodate as many as three sensitizations (two if one conductor is used as a reference). The remaining membrane sensors are similarly connected, but each sensor and its electrical connections can be differently configured. In the example of FIG. 12, electrical connections extend to a substrate edge 1226, but other arrangements can be used. Spacing of the membrane sensors 1201-1209 can be conveniently selected to corresponding to microtiter plate spacings so that microtiter based dispensing and other accessories can be used with the sensor assembly 1200.

Figure 13:
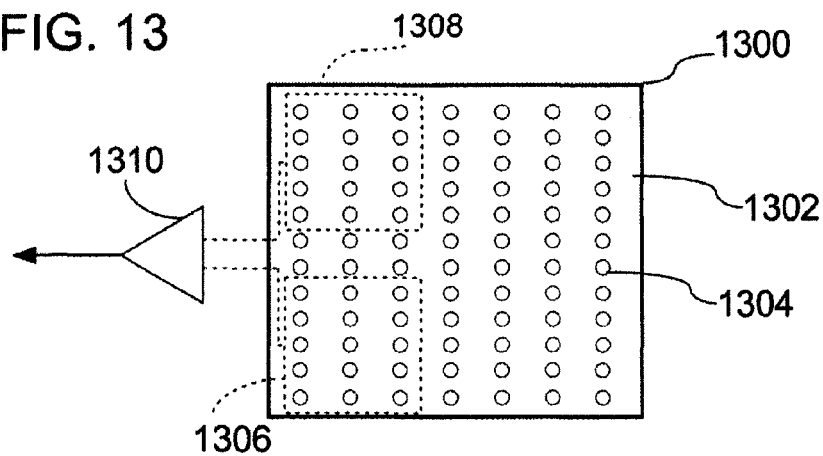
FIG. 13 illustrates a nano-porous membrane on which two sets of nano-pores are coupled to respective conductors.

A representative nano-porous membrane based sensor 1300 is illustrated in FIG. 13. A substrate 1302 is provided with a plurality of nano-pores 1304 or the like. As shown in FIG. 13, the nano-pores are all of the same size and are arranged in a series of rows and columns, but other arrangements of pores of the same or different sizes can be used. Regions 1306, 1308 contain respective pluralities of nano-pores that are electrically connected to a readout amplifier 1310. The readout amplifier is generally a differential amplifier, and produces an output signal based on a difference in an electrical characteristic of the nano-pores in the first region 1306 and the second region 1308. The electrical readout can be processed to obtain, for example, a spectrum (using, for example, a fast Fourier transform), a power spectral density, or to identify a particular spectral component associated with an intended response. The electrical readout can be configured to permit measurement of a time evolution of response so that, for example, spectrum as a function of exposure time is determined.

In view of the many possible embodiments to which the principles of the disclosed technology may be applied, it should be recognized that the illustrated embodiments are only preferred examples and should not be taken as limiting the scope of the invention. For convenience, nano-pore sensitizations for CRP and MPO are described, but other sensitizations are possible such as sensitization for prostate specific antibody or other biomarkers. Therefore, the scope of the invention is defined by the following claims. We therefore claim as our invention all that comes within the scope and spirit of these claims.

We claim:

1. A sensor, comprising:
a solid substrate having a top surface;
a nano-porous membrane situated at the top surface of the solid substrate, the membrane including a plurality of nano-pores that do not extend through the nano-porous membrane, the membrane including a first sensitizing agent for detection of a target compound, the first sensitizing agent being immobilized within a first set of nano-pores, thereby defining a sensitized portion of the membrane;
a first conductor electrically coupled to the first sensitizing agent immobilized in the first set of nano-pores defined in the membrane, the first conductor situated on the top surface of the solid substrate and in contact with the sensitized portion of the membrane, the first conductor outputting an electrical signal associated with detection of the target compound; and
an electrical signal detector for receiving the electrical signal to allow evaluation of the electrical signal following administration of a test specimen to the sensor.

2. The sensor of claim 1, further comprising:
a second conductor electrically coupled to a second set of nano-pores; and
a second sensitizing agent immobilized within the second set of nano-pores.

3. The sensor of claim 2, wherein the first sensitizing agent and the second sensitizing agent are the same.

4. The sensor of claim 2, wherein the first sensitizing agent and the second sensitizing agent are different.

5. The sensor of claim 1, wherein the detector is a spectrum analyzer that is in communication with the first conductor, the spectrum analyzer being configured to produce an estimate of a received signal portion based on a signature frequency or frequencies associated with specific binding of the target compound to the first sensitizing agent.

6. The sensor of claim 5, wherein the spectrum analyzer is configured to produce an estimate of a received signal portion associated with at least two frequencies associated with a detection signature.

7. The sensor of claim 2, wherein the detector is a spectrum analyzer that is selectively coupled to the first conductor and the second conductor, wherein the spectrum analyzer is configured to produce an estimate of a received signal portion associated with a frequency or frequencies associated with a first signature and a frequency or frequencies associated with a second signature.

8. The sensor of claim 7, wherein the spectrum analyzer is configured to produce an estimate of a received signal portion associated with at least two frequencies associated with the first signature.

9. The sensor according to claim 1 wherein the detector is a signature analyzer electrically coupled to the first conductor and configured to estimate a target compound concentration based on at least one signature portion associated with specific binding of the target compound to the sensitizing agent within the first set of nano-pores.

10. The sensor of claim 9, wherein the signature portion is a signal magnitude in a selected frequency range.

11. The sensor of claim 9, wherein the sensor is in communication with a signature database, and the signature analyzer is configured to produce an indication of a presence of at least one target compound based on a comparison of the at least one signature portion associated with specific binding of the target compound by the sensitizing agent with at least one signature stored in the signature database associated with specific binding.

12. An apparatus, comprising:
a base substrate having a plurality of conductor segments defined thereon;
a nano-porous membrane secured to the base substrate, the nano-porous membrane including a plurality of sensitized nano-pores that do not extend through the nano-porous membrane, each nano-pore having a sensitizer for detection of a target compound, the sensitizer being immobilized within the nano-pore, and the sensitizer electrically coupled to a corresponding conductor segment which outputs an electrical signal associated with detection of the target compound;
a fluid chamber for receiving a test fluid and communicating the test fluid to the sensitized nano-pores; and
an electrical signal detector for receiving the electrical signal, thereby allowing evaluation of the electrical signal associated with administration of a test specimen to the sensor.

13. The apparatus of claim 12, wherein the nano-porous membrane is an alumina membrane having a plurality of nano-pores with effective diameters in a range of 5 nm to 500 nm.

14. The apparatus of claim 13, wherein the plurality of nano-pores comprises a first nano-pore having a first effective diameter, and a second nano-pore having a second effective diameter, and wherein the first effective diameter is larger than the second effective diameter.

15. The apparatus of claim 12, wherein the detector is a spectrum analyzer configured to receive electrical signals from the conductor segments and produce spectra of the electrical signals.

16. A method, comprising:
administering a test specimen to a sensor comprising a solid substrate having a top surface, a nano-porous membrane situated at the top surface of the solid substrate, the membrane including a plurality of nano-pores that do not extend through the nano-porous membrane, the membrane including a first sensitizing agent for detection of a target compound, the first sensitizing agent being immobilized within a first nano-pore so as to define a sensitized portion of the membrane, and a first conductor electrically coupled to the first sensitizing agent immobilized in the first nano-pore defined in the membrane, the first conductor situated on the top surface of the solid substrate and in contact with the sensitized portion of the membrane; and
evaluating an electrical signal detector for a detected electrical signal to determine presence or absence of the target compound in the test specimen.

17. The method of claim 16, further comprising:
evaluating a detected electrical signal to identify a magnitude of at least one electrical spectral peak associated with exposure of the sensor to the target compound; and
assessing the test specimen based on the magnitude.

18. The method of claim 16, wherein the test specimen is administered to a sensor sensitized to at least a first target compound and a second target compound.

19. The method of claim 16, wherein the target compound is prostate specific antigen.

20. A method, comprising:
administering a test specimen to a sensor comprising a solid substrate having a top surface, a nano-porous alumina membrane situated at the top surface of the solid substrate, the membrane including a plurality of nano-pores that do not extend through the nano-porous membrane, the membrane including a first sensitizing agent for detection of a target compound, the first sensitizing agent being immobilized within a first set of nano-pores so as to define a sensitized portion of the membrane, and a first conductor electrically coupled to the first sensitizing agent immobilized in the first set of nano-pores defined in the membrane, the first conductor situated on the top surface of the solid substrate and in contact with the sensitized portion of the membrane;

evaluating an electrical signal associated with administration of the test specimen to the sensor; and
assessing the test specimen based on the evaluation.

21. The sensor of claim 7, wherein the spectrum analyzer is configured to produce an estimate of a received signal portion associated with at least two frequencies associated with the first signature and at least two frequencies associated with the second signature.

22. The apparatus of claim 12, further comprising a first set of sensitized nano-pores, the first set of nano-pores having a first sensitizer for detection of a first target compound.

23. The apparatus of claim 22, further comprising a second set of sensitized nano-pores, the second set of nano-pores having a second sensitizer for detection of a second target compound.

24. The method of claim 16, wherein the first sensitizing agent is immobilized within a first set of nano-pores, and the first conductor is electrically coupled to the first sensitizing agent immobilized in the first set of nano-pores.

\* \* \* \* \*